(12) United States Patent
Ehwald et al.

(10) Patent No.: US 6,938,463 B2
(45) Date of Patent: Sep. 6, 2005

(54) METHOD FOR AFFINITY VISCOSIMETRY AND VISCOSIMETRIC SENSOR

(75) Inventors: Rudolf Ehwald, Berlin (DE); Ulrich Haueter, Grosshoechstetten (CH); Uwe Beyer, Bern (CH)

(73) Assignee: Disetronic Licensing AG, Burgdorf (CH)

( * ) Notice: Subject to any disclaimer, the term of this patent is extended or adjusted under 35 U.S.C. 154(b) by 468 days.

(21) Appl. No.: 10/232,969

(22) Filed: Aug. 30, 2002

(65) Prior Publication Data

US 2003/0054560 A1 Mar. 20, 2003

Related U.S. Application Data

(63) Continuation of application No. PCT/CH01/00126, filed on Feb. 28, 2001.

(30) Foreign Application Priority Data

Mar. 3, 2000 (DE) .......................... 100 10 539

(51) Int. Cl.$^7$ ............................................. G01N 19/08
(52) U.S. Cl. ..................... 73/54.06; 73/54.01; 73/53.01
(58) Field of Search ............................ 73/54.06, 54.01, 73/53.01

(56) References Cited

U.S. PATENT DOCUMENTS

| | | | |
|---|---|---|---|
| 3,808,877 A | | 5/1974 | Blair |
| 4,286,457 A | | 9/1981 | Johnson, Jr. |
| 4,786,034 A | * | 11/1988 | Heess et al. ............. 267/64.15 |
| 4,972,701 A | | 11/1990 | Yau |
| 6,210,326 B1 | | 4/2001 | Ehwald |
| 6,267,002 B1 | | 7/2001 | Ehwald et al. |
| 6,477,891 B2 | * | 11/2002 | Ehwald et al. ............. 73/54.01 |
| 6,627,075 B1 | * | 9/2003 | Weissgerber et al. .... 210/198.2 |

* cited by examiner

Primary Examiner—Hezron Williams
Assistant Examiner—Rodney Frank
(74) Attorney, Agent, or Firm—Dorsey & Whitney LLP

(57) ABSTRACT

A method and apparatus for determining solute levels by affinity viscosimetry involving a sensitive fluid, in which the sensitive fluid flows continuously through a first hydraulic resistor in the flow direction of the dialysis chamber, and the sensitive fluid modified by dialysis simultaneously flows through another resistor, wherein the pressure differences between the resistors is determined on-line with the aid of pressure sensors and converted into a relative value which is approximately proportional to the concentration of solute.

20 Claims, 2 Drawing Sheets

METHOD FOR AFFINITY VISCOSIMETRY AND VISCOSIMETRIC SENSOR

PRIORITY CLAIM

This application is a Continuation of International Patent Application PCT/CH01/00126, filed on Feb. 28, 2001, which claims priority to German Application No. DE 100 10 539 A1, filed on Mar. 3, 2000, both of which are incorporated herein by reference.

BACKGROUND

For measuring blood sugar concentration, viscosimetric affinity sensors have, among other things, been developed which can be miniaturized and used in an implanted form (DE 195 01 159) or as transdermal sensors (DE 197 14 087).

Viscosimetric affinity sensors for determining sugar levels are based on a sensitive fluid, a concentrated solution consisting of macromolecular branched dextran and the tetravalent bonding protein concanavalin A (ConA), with the specificity of glucose, being situated in a dialysis chamber coupled to a device for measuring viscosity. The viscosity of the sensitive fluid is high when the dextran molecules are cross-linked via their exposed terminal glucose groups by ConA, and is reduced, dependent on concentration, with the free glucose penetrating the dialysis chamber by diffusion from a glycosuric external solution.

A particularly favorable method of affinity viscosimetry involves measuring the viscosity, once dialysis has been performed in the segment of a microdialysis fiber, by measuring the flow resistor of a downstream capillary (DE 197 14 087). A known problem in affinity viscosimetry is that the viscosity of the sensitive fluid is dependent not only on the concentration of glucose but to a large extent also on the temperature and on the concentration of the active glycopexic protein (Ballerstädt and Ehwald, Biosensors & Bioelectronics 9: 557–567, 1994; Ehwald et al., Analytical Biochemistry 234: 1–8, 1996). In order to release the signals of a viscosimetric affinity sensor for glucose from this significant temperature-dependency, relative values having low temperature-dependency can be formed (Ballerstädt and Ehwald, Biosensors & Bioelectronics 9: 557–567, 1994). Up until now, only methods for discontinuously determining the relative values by consecutively measuring the viscosity changed by glucose and the reference viscosity have been known. A method for continuously determining such relative values in a sensor on-line has not been known up until now.

Developing a viscosimetric affinity sensor which operates on-line requires a method for preparing readings which converts viscosity-dependent measured values provided by the sensor on-line into glucose concentration. In this connection, the aim is that the sensor detects a measured value which is directly dependent, in a linear relationship, on the glucose concentration and is simultaneously independent of the temperature and the concentration of active ConA in the sensitive fluid. The method to this effect has not been known up until now.

SUMMARY

An object of the invention is to provide a method and a sensor for determining sugar levels by affinity viscosimetry, which allow a parameter which is largely independent of the temperature and the concentration of ConA and directly proportional to the concentration of sugar to be detected on-line.

The object is addressed by the method for affinity viscosimetry and by a viscosimetric sensor in accordance with the present invention.

In one embodiment, the present invention comprises a method and apparatus for determining solute levels by affinity viscosimetry involving a sensitive fluid, in which the sensitive fluid flows continuously through a first hydraulic resistor in the flow direction of the dialysis chamber, and the sensitive fluid modified by dialysis simultaneously flows through another resistor, wherein the pressure differences between the resistors is determined on-line with the aid of pressure sensors and converted into a relative value which is approximately proportional to the concentration of solute.

In one embodiment, the present invention comprises a method and apparatus for determining sugar levels by affinity viscosimetry, in which the sensitive fluid flows continuously through a first hydraulic resistor in the flow direction of the dialysis chamber, and the sensitive fluid modified by dialysis simultaneously flows through another resistor, wherein the pressure differences between the resistors is determined on-line with the aid of pressure sensors and converted into a relative value which is approximately proportional to the concentration of sugar.

In accordance with the invention, it is advantageous if the sensitive fluid flows continuously, having a defined sugar content or having no sugar content, through a hydraulic resistor in the flow direction of the dialysis chamber, the reference resistor, and the sensitive fluid modified by dialysis simultaneously flows through another resistor which is approximately isothermal with the reference resistor, the measuring resistor, wherein the pressure difference which drops away across the reference resistor and the measuring resistor is determined on-line with the aid of pressure sensors and converted into a relative value approximately proportional to the concentration of sugar.

DETAILED DESCRIPTION

Figure 1:
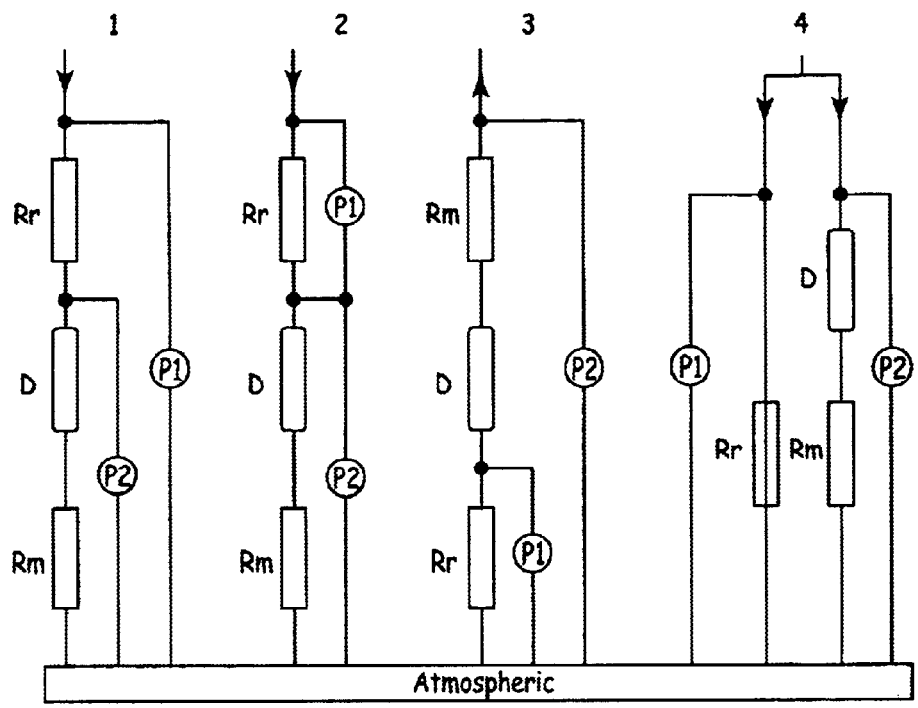
FIG. 1 depicts possible variants for the arrangements of the resistors in a sensor in accordance with the invention.

FIG. 1 schematically shows a few of the possible variants for the arrangements of the resistors, the dialysis chamber and the pressure sensors needed for measuring. The arrow represents the pressure pump (Variants 1, 2 and 4) or suction device (Variant 3) with the generated flow direction of the sensitive fluid or solution.

The reference resistor Rr, the dialysis chamber D and the measuring resistor Rm can lie in succession on a flow path (FIG. 1, Variants 1 to 3), or the reference resistor lies on one flow path and the dialysis chamber and the measuring resistor lie together on a parallel flow path (FIG. 4, Variant 4).

If the reference resistor and the measuring resistor lie on one flow path, one pump or suction device is sufficient, and the drop in pressure across the two resistors can be detected by a suitable arrangement of pressure sensors P1 and P2 (FIG. 1, Variants 1 to 3). If the reference resistor and the measuring resistor lie on two parallel flow paths, they are connected in accordance with the invention to one or more pump or suction devices which maintain a constant relation between the flows on the two flow paths (FIG. 1, Variant 4).

To simultaneously measure the drop in pressure across the reference resistor and the drop in pressure across the flow resistor, pressure sensors can be suitably arranged on the flow path, wherein the deformable membranes of these pressure sensors must lie either between the atmosphere and a measuring point on the flow path (FIG. 1, Variants 1, 3 and 4) or between two different measuring points on the flow path (P1 in FIG. 1, Variant 2).

If the measuring resistor and the reference resistor are measured simultaneously, the ratio of measuring resistor and reference resistor is known to provide a relative, temperature-dependent viscosity (Ballerstädt and Ehwald, Biosensors & Bioelectronics 9: 557–567, 1994), which does not, however, decrease linearly with the glucose concentration and is not suitable for calculating glucose levels from the measured resistor values in a sensor. The relative fluidity ("RF") calculated in accordance with the invention therefore represents the quotient between the drop in pressure at the reference resistor and the sum of the drop in pressure at the measuring resistor and a correction value leading to a linearization of the correlation with the glucose concentration. The relative fluidity is a relative value which is independent of temperature and ConA concentration and which has a linear relationship to the glucose concentration.

It is important for forming the temperature-independent relative value for the flow resistors cited to be kept isothermal. This may be achieved by contacting the two resistors with the body or with an additionally temperature-stabilized device, or by having the two resistors in joint contact with a good heat conductor. For the method in accordance with this embodiment, it is furthermore necessary for the expandable volume content of the flow path between the reference resistor and the measuring resistor to be smaller than the volume of sensitive fluid moved by the pump or suction device within a particular period of time corresponding to the measuring task, since otherwise the change in pressure at the measuring resistor responds too slowly to the change in viscosity. This period of time should not be longer than 15 minutes.

Figure 2:
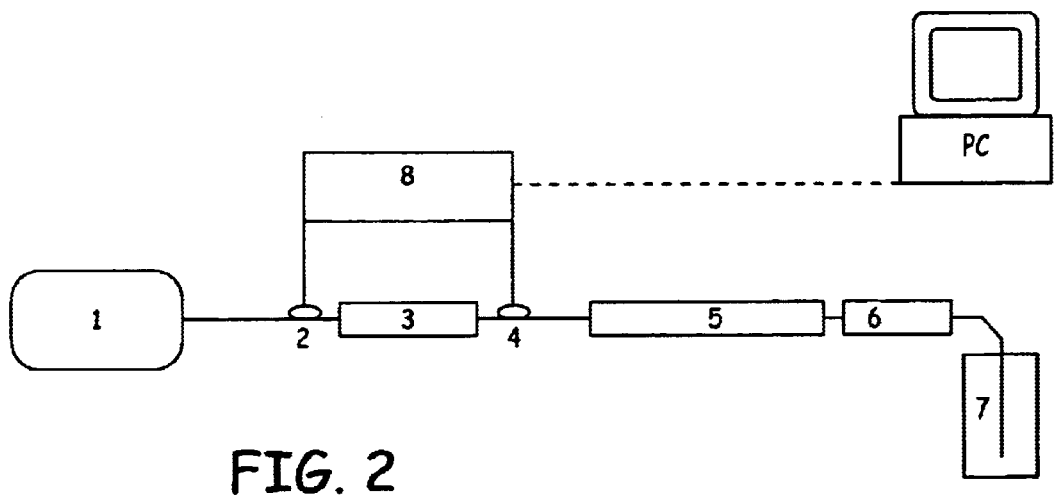
FIG. 2 is a schematic representation of a sensor in accordance with the invention for determining sugar levels by affinity viscosimetry.

Exemplary Application:

In the equipment shown in FIG. 2, sensitive fluid is moved through a flow channel at a constant speed (5 µl/h) by means of a pump, wherein a pressure sensor for measuring the pressure p1, the hydraulic reference resistor 3, a pressure sensor 4 for measuring the pressure p2, a dialysis probe 5, the hydraulic measuring resistor 6 and a collecting vessel 7 for the used sensitive fluid are situated in succession on said flow channel. In short intervals, the pressures p1 and p2 are measured simultaneously and stored, assigned to the time of measurement, by means of a programmable evaluation unit 8. The difference p1–p2 is then the drop in pressure across the reference resistor, and p2 the drop in pressure across the measuring resistor. From these pressure values, the evaluation unit calculates the relative fluidity and/or, with the aid of settable constant calibration parameters, the glucose concentration, and displays this on a display.

Figure 3A:
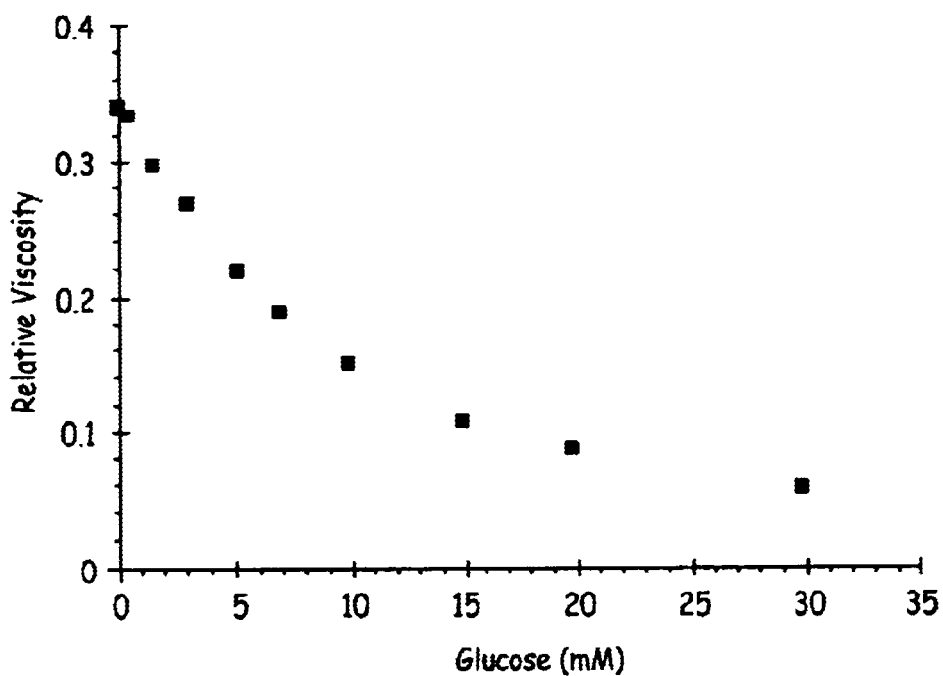
FIGS. 3a and 3b are diagrams showing relative viscosity and relative fluidity against glucose concentration.
Figure 3B:
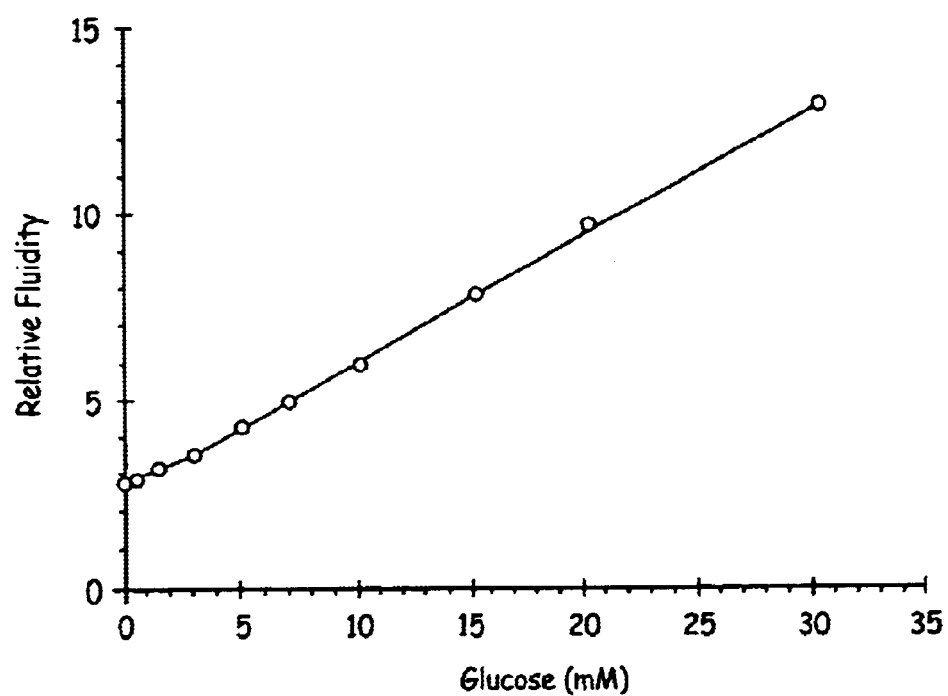

If the quotient Q is the ratio of the drop in pressure across the reference resistor to the drop in pressure across the measuring resistor, RF may be calculated according to the formula:

$$RF=Q/(1+kQ) \quad \text{(Equation 1)}$$

where the constant k is a linearization parameter dependent on the sensitive fluid and the ratio of the resistors, and is determined iteratively for the best correlation between the RF values and the corresponding values of a glucose concentration series (FIG. 3b). As opposed to the relative viscosity (FIG. 3a), the relative fluidity defined by Equation 1 is proportional to the glucose concentration.

In the foregoing description embodiments of the invention have been presented for the purpose of illustration and description. They are not intended to be exhaustive or to limit the invention to the precise form or steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A method for determining sugar levels by affinity viscosimetry involving a sensitive fluid, in which the sensitive fluid flows continuously through a first hydraulic resistor in the flow direction of the dialysis chamber, and the sensitive fluid modified by dialysis simultaneously flows through another hydraulic resistor, wherein the pressure differences between the resistors is determined on-line with the aid of pressure sensors and converted into a relative value which is approximately proportional to the concentration of sugar.

2. The method as set forth in claim 1, wherein said fluid exhibits one of a defined sugar content and no sugar content.

3. The method as set forth in claim 1, wherein said first resistor is a reference resistor and said another resistor is a measuring resistor which is approximately isothermal with said reference resistor, wherein the pressure difference which drops away across said measuring resistor and said reference resistor is determined.

4. The method as set forth in claim 3, wherein said reference resistor, said dialysis chamber and said measuring resistor are in succession on a flow path.

5. The method as set forth in claim 3, wherein said reference resistor is on one flow path and said dialysis chamber and said measuring resistor are together on a parallel flow path.

6. The method as set forth in claim 3, wherein the relative value represents the quotient between the drop in pressure at said reference resistor and the sum of the drop in pressure at said measuring resistor and a correction value leading to a linearization of the correlation with the glucose concentration.

7. A method for determining solute levels by affinity viscosimetry involving a sensitive fluid, in which the sensitive fluid flows continuously through a first resistor in the flow direction of the dialysis chamber, and the sensitive fluid modified by dialysis simultaneously flows through another resistor, wherein the pressure differences between the resistors is determined on-line with the aid of pressure sensors and converted into a relative value which is approximately proportional to the concentration of solute.

8. The method as set forth in claim 7, wherein said first resistor is a reference resistor and said another resistor is a measuring resistor which is approximately isothermal with said reference resistor, wherein the pressure difference which drops away across said measuring resistor and said reference resistor is determined.

9. The method as set forth in claim 8, wherein the relative value represents the quotient between the drop in pressure at said reference resistor and the sum of the drop in pressure at said measuring resistor and a correction value leading to a linearization of the correlation with the solute concentration.

10. A device for determining solute concentration by affinity viscosimetry involving a sensitive fluid, comprising a first resistor in the flow direction of a dialysis chamber which the sensitive fluid continuously flows through, another resistor which the sensitive fluid modified by dialysis simultaneously flows through, at least one pressure sensor which determines the pressure difference between said resistors on-line, and means for converting the pressure difference to a relative value approximately proportional to the concentration of solute.

11. A sensor for determining sugar levels by affinity viscosimetry involving a sensitive fluid, comprising a first hydraulic resistor in the flow direction of a dialysis chamber which the sensitive fluid continuously flows through, another hydraulic resistor which the sensitive fluid modified by dialysis simultaneously flows through, pressure sensors which determine the pressure differences between said resistors on-line, and a device by means of which the pressure differences are converted into a relative value which is approximately proportional to the concentration of sugar.

12. The sensor as set forth in claim 11, further comprising one of a continuously conveying pump or suction device which is coupled to a flow path with at least two pressure sensors, on which flow path said first hydraulic resistor, the dialysis chamber and the another hydraulic resistor are arranged in succession in the flow direction, wherein the flow resistors are in joint contact with one of a person's body, a temperature-stabilized device or a heat conductor, and the expandable volume content of the flow path between said first hydraulic resistor and said another hydraulic resistor is smaller than the volume of sensitive fluid moved by the pump or suction device within 15 minutes.

13. The sensor as set forth in claim 11, further comprising two parallel flow paths coupled to one or more pump or suction devices which maintain a constant relation between the flows on the two flow paths; said first hydraulic resistor on one flow path and said dialysis chamber and said another hydraulic resistor on the other flow path, said another hydraulic resistor downstream of the dialysis chamber; a pressure sensor arranged on each of the two flow paths for measuring the drop in pressure across the respective flow resistors, wherein the resistors are in joint contact with one of a person's body, a temperature-stabilized device or a heat conductor.

14. The sensor as set forth in claim 12, wherein a deformable membrane of the pressure sensors lies between the atmosphere and a suitable measuring point on the flow path, so measuring the drop in pressure across said resistors.

15. The sensor as set forth in claim 13, wherein a deformable membrane of the pressure sensors lies between suitable points on the flow paths, so measuring the drop in pressure across said resistors.

16. A device for determining sugar levels by affinity viscosimetry involving a sensitive fluid, comprising a first resistor through which the sensitive fluid flows, a dialysis chamber through which the sensitive fluid flows, another resistor through which the sensitive fluid modified by dialysis simultaneously flows, at least one pressure sensor which determines the pressure difference between said resistors on-line, and means for converting the pressure difference to a relative value approximately proportional to the sugar level.

17. The device as set forth in claim 16, further comprising one of a continuously conveying pump or suction device which is coupled to the flow path of the sensitive fluid, on which flow path first resistor, the dialysis chamber and the another resistor are arranged in succession in the flow direction.

18. The device according to claim 17, wherein the resistors are in contact with one of a person's body, a temperature-stabilized device or a heat conductor.

19. The device according to claim 16, further comprising two parallel flow paths coupled to one or more pump or suction devices, said first resistor on one flow path and said dialysis chamber and another resistor on the other flow path, said another resistor downstream of said dialysis chamber, and a pressure sensor associated with each of the flow paths for measuring the drop in pressure across the respective resistors.

20. The device according to claim 19, wherein the resistors are in contact with one of a person's body, a temperature-stabilized device or a heat conductor.

* * * * *